July 11, 1950 P. R. WHITTIER Plant Pat. 962
GAILLARDIA PLANT
Filed Oct. 16, 1948
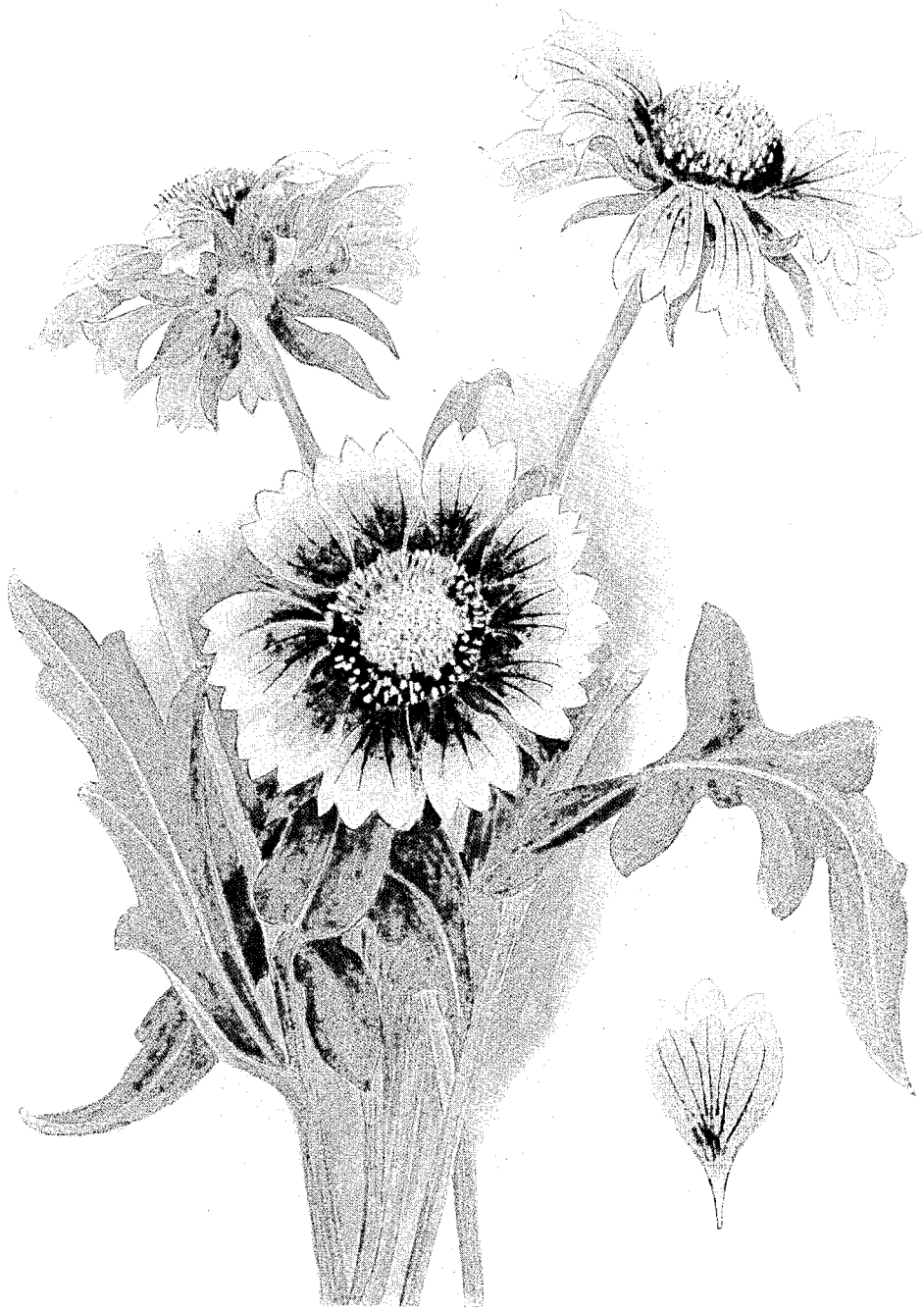
WITNESS
Addison E. Avery
INVENTOR
Paul R. Whittier,
by: John H. Leonard,
his ATTY.

Patented July 11, 1950 Plant Pat. 962

UNITED STATES PATENT OFFICE

962

GAILLARDIA PLANT

Paul R. Whittier, Beverly, Mass., assignor to
John J. Grullemans, Mentor, Ohio

Application October 16, 1948, Serial No. 54,916

1 Claim. (Cl. 47—60)

This invention relates to a new and distinct variety of gaillardia plant, and particularly to a *Gaillardia aristata* Grandiflora variety.

The new variety is illustrated in the drawing which in the large view illustrates the terminals of three main stalks, each with a bloom thereon, and portions of two stalks nearer the base with the leaves thereon, and in the lower right hand view, a single petal full size.

The present variety was obtained by crossing a gaillardia seedling, identified in my records as No. X57, as the seed parent and gaillardia Mrs. Turner, an English named variety, as the pollen parent. Seedling No. X57 was one selected from a number of seedlings which I had developed as a result of reproducing several generations, in turn, from seedlings.

The plant was first developed and grown by me in 1939 in Beverly, Massachusetts, and was asexually reproduced by me from root cuttings.

The root structure of the plant is rather fibrous and coarse, the root being relatively large for this type of plant and somewhat shallow but with the usual lateral spread. The resistance of the root to disease and drought is exceptional and its resistance to wetness is good. The winter resistance of the root is very good when it is protected and is good even when not protected, it having withstood winters in localities where the temperature was as low as 15 degrees below zero, Fahrenheit. Generally the roots are less hardy in very wet soil than in the lighter dry soils.

The exposed plant is herbaceous, upright and generally bushy, reaching a height of about four feet during the main flowering portion of its life, this being quite an unusual size for this type of plant. The general shape or contour of the exposed plant is usual for gaillardias.

The plant is very vigorous in its growth. The exposed portion of the plant has exceptional resistance to low temperature when protected and very good resistance when unprotected. Its resistance to disease and drought also is exceptional. It withstands wet seasons well. The plant prefers, for the best growth, a moderate to intense sun and is rather indifferent as to exposure. It thrives well in any normally well drained ordinary garden soil.

The main stalks are upright, herbaceous and much branched. For a gaillardia plant they are relatively stiff and tough. In general the new growth of stalks is of a green color such as is usual for gaillardias while the old growth is of the usual green tinged with red. The color is uniform on both the new and old growth. The main stalks vary in length from 2½ feet to 4 feet and grow in the usual manner from the roots. Their surface texture is usual, being slightly fuzzy. The branches generally are alternate. The main stalks at the top end are generally green, tinged with red, comparable to Maerz and Paul Chart Pl. 14–B2, this color shading into a color comparable to Maerz and Paul Chart Pl. 14–K1.

The foliage is generally open, the leaves being arranged in alternate fashion. Both the new leaves and old leaves are of the usual Gaillardia green on top, and are slightly lighter on the bottom, the color being generally uniform. The leaves are quite large having a maximum length of about 12 inches and a minimum length of about 4 inches. They vary in width from 3 inches to ¾ inch. The leaves are of about average thickness and are slightly fuzzy on both the upper and lower faces. Generally in color they are a grey-green, comparable to Maerz and Paul Chart Pl. 23–E5. Their persistency on the plant is good but they are characterized mostly by their large size. The peticles of the leaf stems are green tinged with red. They are of the usual length and fuzzy surface texture and are very strong.

The plant thrives and blooms well in most sections of the United States though it seems to prefer the Eastern coast and Western coast for the best blooms. It prefers a rich loam. It produces the best quality blooms in a sunny exposure in well drained but moist and neutral soil. Too dry a season results in flowers which are somewhat smaller and lighter in color. On the other hand too much shade causes a reduction in the size and strength of the flowers. Either too dry or too shady a location reduces the number of the flowers.

The blooming period is generally from about June to October during which period the plant blooms continuously. Cutting of the flowers produces better new blooms, whereas if they are not cut, fewer new blooms are produced.

The buds are of the usual shape though somewhat larger than is usual. They are borne upright and are generally a dark red with yellow tips when the petals begin to unfurl, this color changing to a brighter dark red with yellow tips when the flower is half blown. The sepals are usual and the calyx is of the usual shape but very large. Its color is comparable to Maerz and Paul Chart Pl. 22–H6. The rate of blooming is affected somewhat by the weather, the buds opening slowly in cold weather and very rapidly during hot dry spells. The blooms of the main group are generally from 4 inches to 5½ inches in diameter and average about eight per plant. They are borne singly on long peduncles and they have a good permanence, lasting several days on the plant or when cut. The blooms have from about eleven to seventeen petals each. The petals, at their outer ends are a yellow color comparable to Maerz and Paul Chart Pl. 9–L6. There is a sharp line of demarcation between the yellow color of the outer ends of the petals and the main body thereof. Next adjacent the yellow outer ends, the color is brownish red, comparable to Maerz and Paul Chart Pl. 4–K10. This shades gradually into darker brownish red toward the base, beginning with a color comparable to Maerz and Paul Chart Pl. 4–L9 and merging into a color comparable to Maerz and Paul Chart Pl. 7–H6.

The center of the flower is in the form of a disc, the edge or outer portion of which is a brownish red comparable to Maerz and Paul Chart Pl. 7–L6, the center of the disc being of a yellow comparable to Maerz and Paul Chart Pl. 12–L9. The reverse of the petals is about the same shade as the upper face though somewhat lighter.

The sepals are grayish green comparable to Maerz and Paul Chart Pl. 22–H6.

The general tonality of the bloom at a distance is orange-red with yellow edges. The bloom tends to lighten in shade slightly after about the end of the second day after blooming. The petals are of smooth texture and of the usual form and arrangement. The flower as a whole is of the usual shape but very large. It has the usual fragrance which is of average strength and quality and which has medium lasting qualities both in a cut and an uncut flower.

The stamens are composite and the filaments relatively short and generally of an orange-yellow color. The pollen is of a color comparable to Maerz and Paul Chart Pl. 10–L8. The styles generally are small and light green and the stigma small and brownish red. The ovaries generally are sparse. The fruit is of the usual form, abundance and color.

The plant is distinguished particularly for its giant over-all size and the extremely large size of the flowers. Another pertinent characteristic is the unusual shade of the deep brownish red and yellow colors of the flowers.

Having fully shown and described my new variety of gaillardia plant and its mode of asexual reproduction, I claim:

A variety of gaillardia plant herein shown and described, characterized by its giant over-all size, the large size of the flower, and the unusual shade of the deep brownish red and yellow colors of the flowers.

PAUL R. WHITTIER.

No references cited.